United States Patent
Kanel et al.

(10) Patent No.: US 7,541,499 B2
(45) Date of Patent: Jun. 2, 2009

(54) PROCESS FOR THE RECOVERY OF PHOSPHORUS AND IODINE CONTAINING CATALYST COMPONENTS

(75) Inventors: Jeffrey Scott Kanel, Hurricane, WV (US); Stanley John Okrasinski, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 6 days.

(21) Appl. No.: 11/702,853

(22) Filed: Feb. 6, 2007

(65) Prior Publication Data

US 2007/0142674 A1   Jun. 21, 2007

Related U.S. Application Data

(62) Division of application No. 10/739,785, filed on Dec. 18, 2003, now Pat. No. 7,196,227.

(51) Int. Cl.
   *C07F 9/02* (2006.01)
(52) U.S. Cl. .............................. 568/9; 568/8
(58) Field of Classification Search ............ 568/9, 568/8
See application file for complete search history.

(56) References Cited

U.S. PATENT DOCUMENTS

| | | | | |
|---|---|---|---|---|
| 2,683,169 A | * | 7/1954 | Jensen et al. | 562/817 |
| 4,440,570 A | * | 4/1984 | Erpenbach et al. | 75/413 |
| 4,556,644 A | * | 12/1985 | Erpenbach et al. | 502/33 |
| 5,399,752 A | * | 3/1995 | Okrasinski et al. | 562/608 |
| 6,303,830 B1 | * | 10/2001 | Argyropoulos et al. | 568/454 |
| 6,307,180 B1 | * | 10/2001 | Arx et al. | 219/217 |

* cited by examiner

*Primary Examiner*—Sikarl A Witherspoon
*Assistant Examiner*—Chukwuma O Nwaonicha
(74) *Attorney, Agent, or Firm*—Brett L Nelson; Bernard J. Graves, Jr.

(57) ABSTRACT

Disclosed is a process for the recovery of phosphorus and/or iodine containing catalyst components, present as an organophosphorus compound such as trihydrocarbylphosphine compounds and tetrahydrocarbylphosphonium compounds, from a solution of at least one such organophosphorus compound in an organic solvent by the steps comprising (1) converting the organophosphorus compound to an iodide complex of a organophosphonium compound which is insoluble in the organic solvent; and (2) separating the insoluble iodide complex of the organophosphonium compound from the solution. The process also results in the recovery of iodine values present in the solution.

10 Claims, No Drawings

PROCESS FOR THE RECOVERY OF PHOSPHORUS AND IODINE CONTAINING CATALYST COMPONENTS

This application is a divisional of U.S. patent application Ser. No. 10/739,785 filed on Dec. 18, 2003, now U.S. Pat. No. 7,196,227 the disclosure of which is incorporated herein by reference in its entirety.

This invention pertains to a process for the recovery of phosphorus and/or iodine containing catalyst components from solutions employed in catalytic chemical processes such as carbonylation processes. More specifically, this invention pertains to a process for the recovery of an organophosphorus compound such as trihydrocarbylphosphine compounds and tetrahydrocarbylphosphonium compounds from a solution of at least one such organophosphorus compound in an organic solvent by the steps comprising (1) converting the organophosphorus compound to an organophosphonium compound which is insoluble in the organic solvent; and (2) separating the insoluble organophosphonium compound from the solution.

Acetic acid traditionally has been manufactured by methods that rely upon the oxidation of either light hydrocarbons or ethylene-derived acetaldehyde. More recently, however, the homogeneously-catalyzed carbonylation of methanol has proven to be the process of choice for the commercial production of acetic acid and, as a result, virtually all new manufacturing capacity makes use of this technology. This process typically employs a rhodium compound and various promoters to convert a mixture of methanol (or one of its derivatives such as methyl iodide) and carbon monoxide to acetic acid (U.S. Pat. No. 3,769,329). The use of such an expensive Group VIII noble metal catalyst system imposes two important requirements upon any commercial facility which utilizes rhodium: (1) as much acetic acid as possible must be produced per unit of time for each unit of rhodium-containing catalyst present in the reactor (high turn-over and high rate), and (2) a means must be provided to rigorously recover and recycle any rhodium which escapes the confines of the reactor. Adherence to these constraints helps to assure that the lowest catalyst cost possible per unit of acetic acid produced will be attained.

To maximize the productivity of rhodium-based processes, substantial effort has been expended to identify promoters and reaction conditions that optimize the behavior of the rhodium-based catalyst systems. In addition, techniques for the recovery and recycle of catalyst residues have been developed and implemented. Even more importantly, however, technology that avoids the use of an expensive noble metal catalyst system has been developed and exhibits several benefits over its rhodium-based predecessors. Such benefits include, in part, (1) a substantial reduction in initial capital investment for the construction of a commercial manufacturing facility can be realized by avoiding the purchase of large quantities of a precious metal; (2) a further reduction in initial capital outlay occurs if the need for a rigorous catalyst recovery scheme is minimized; and (3) the recurring costs associated with the operation of these recovery and recycle units can be minimized. These benefits represent a significant simplification and improvement in process technology.

Attempts to improve the efficiency of both noble and non-noble metal-containing catalyst systems useful in carbonylation processes has led to the development of catalysts which contain both iodine and phosphorus compounds. See, for example, U.S. Pat. Nos. 4,661,631, 4,659,518, 4,356,320, 4,218,340 and 5,352,813; PCT Published Patent Application WO 92/04118; and M. J. Baker et al., *J. Chem.Soc., Chem. Commun.* 1995, (2), 197-198. The phosphorus compounds typically are charged to the reactor as an organophosphine compound. The organophosphine compounds may be converted in the reactor to a phosphonium iodide salt as a result of the in situ reaction of the organophosphine and an alkyl iodide. Alternatively, a phosphonium iodide salt may be charged directly to the reactor. The presence of these promoters provides a number of benefits such as increased rates of reaction, increased selectivity, and/or a decrease in the volatility of key catalyst components, depending upon the catalyst system with which they are employed. Providing a simple method for the recovery and reuse of the phosphorus and iodine content of catalyst solutions would increase the utility of such processes. Indeed, for catalyst systems which utilize a non-noble (rather than a noble) metal, the iodine and phosphorus components may represent the bulk of the value of the catalyst. For noble metal-containing catalyst systems, the use of unusual and difficult to obtain phosphorus compounds may require that they be recovered. For either type of catalyst system, the recovery and reuse of the iodine and phosphorus catalyst components may be of economic benefit and/or simplify the disposal of spent or purged catalyst solutions. As noted however, it is imperative that any method for the recovery of catalyst components other than noble metals be particularly simple and economical.

The recovery of various catalyst components from carbonylation catalyst mixtures that contain a non-noble metal Group VIII component (nickel) is described in the literature, e.g., U.S. Pat. No. 4,988,652.

Another method, described in U.S. Pat. No. 3,132,177, relies upon the recovery of substantial quantities of the nickel component of the catalyst as the volatile nickel tetracarbonyl. Such a treatment is both difficult and inconvenient. Again, there is no indication that the method provides any means for the removal of any unwanted impurities before the catalyst components are reused. Furthermore, the catalyst system described does not contain any organophosphorus compound.

U.S. Pat. No. 3,132,177 describes a process for the recovery of catalyst components from a crude, liquid product obtained from the carbonylation of methanol to acetic acid. The catalyst employed in the carbonylation process consists of nickel and iodine compounds. Volatile catalyst components (nickel tetracarbonyl and methyl iodide) are stripped from the crude liquid product by passage of a gas through the mixture. The volatile components are then recovered from the gas stream by absorption in methanol. The remaining crude product stream is concentrated and the residue solution or slurry is recycled to the reactor.

Japanese Patent Publication JP 62,072645 [*Chem. Abstr.* 107:136317] discloses a process for recovering nickel, tin, lithium and iodine compounds from reaction tars resulting from the simultaneous production of acetic anhydride and acetic acid.

In the case of rhodium-containing carbonylation catalyst systems, one or two practical considerations usually are of major importance in the recovery of catalyst components. The first major consideration is the recovery of the rhodium component since it is almost always the most valuable material present. The second consideration is the removal of corrosion metals as they are known to inhibit the rate of catalysis for a number of rhodium-containing catalyst systems. Procedures which provide for the recovery of catalyst components such as organophosphorus compounds from rhodium-containing catalyst combinations have been published. For example, U.S. Pat. No. 5,124,290 discloses a process for removing metallic corrosion products from carbonylation catalysts used under anhydrous conditions. The catalyst system comprises a Group VIII noble metal, an iodide or bromide, an organophosphonium or organoammonium salt and, optionally, lithium. The procedure accomplishes the recovery of the noble metal and organophosphonium or organoammonium salt by separating these materials from the reaction solution using an ion-exchange resin through a series of adsorption and desorption.

Extraction is a commonly utilized method when the contaminated catalyst solutions contain organic impurities, e.g., reaction tars. Some of these methods offer little capability to remove corrosion metals from the catalyst solution and would require operation in conjunction with additional methods. A significant drawback of such methods is the multiple extraction/separation steps usually required. U.S. Pat. No. 5,047,377 discloses the removal of impurities from a contaminated catalyst solution which contains rhodium, organic and/or inorganic promoters (which may include organophosphonium or organoammonium salts), organic impurities and products by extraction with a liquefied or supercritical gas. The extractant removes the organic impurities. U.S. Pat. No. 5,002,914 discloses a method of treating catalyst solutions similar to those of U.S. Pat. No. 5,047,377 with a trialkylphosphine extractant to extract the rhodium content. The remaining solution, now free of rhodium carbonyl compounds, is subjected to further purification by extraction.

U.S. Pat. No. 4,985,383 discloses a precipitation/extraction technique for the recovery of catalyst components from catalyst solutions similar to those disclosed in U.S. Pat. No. 5,047,377. The addition of water to the catalyst solution causes precipitation of the rhodium component along with any undistillable organic fraction. The aqueous phase containing an organic promoter comprising an organophosphonium or organoammonium salt and corrosion metals then is extracted with an alcohol to remove the organic promoter and the remaining aqueous phase containing the corrosion metals may be discarded. Removal of the alcohol extractant by evaporation allows the recovery of the organic promoter. The precipitated rhodium and undistillable organic fraction are combined with the recovered organic promoter and then recycled into the process.

A catalyst solution similar to that of U.S. Pat. No. 5,047,377 but used for the carbonylation of methyl acetate and/or dimethyl ether is extracted with a dialkylether and an alkanol according to a process disclosed in U.S. Pat. No. 4,746,640. The undistillable organic contaminants along with portions of acetic anhydride, acetic acid and/or ethylidene diacetate enter the ether phase. The ether phase is separated and treated with iodine or methyl iodide; the resulting precipitated promoter-containing catalyst complex can be combined with the purified catalyst solution obtained in the first step. Several subsequent steps recover the various fractions for reuse or disposal. Also see U.S. Pat. No. 4,629,711 for a similar process.

The patent literature provides many additional examples of extractive processes, e.g., U.S. Pat. Nos. 5,364 822, 5,100, 850, and 4,945,075 and WO 91/07372; precipitation, e.g., U.S. Pat. Nos. 4,131,640 and 4,434,240; and distillation, either alone or in combination with another method, e.g., U.S. Pat. No. 4,650,649 and 4,628,041.

We have discovered a novel means for the recovery of iodine-containing components and organophosphorus compounds from organic solutions thereof by converting the organophosphorus compounds to insoluble organophosphonium compounds. Therefore, the present invention in its broader aspects provides a process for the recovery of an iodine-containing component and organophosphorus compound, such as trihydrocarbylphosphine compounds and tetrahydrocarbylphosphonium compounds, from a solution of at least one such organophosphorus compound in an organic solvent by the steps comprising (1) converting the organophosphorus compound to an organophosphonium compound which is insoluble in the organic solvent; and (2) separating the insoluble organophosphonium compound from the solution. Another embodiment of our invention involves a process for the recovery of an organophosphonium compound, preferably an organophosphonium iodide, from a solution of the—organophosphonium compound in an organic solvent by the steps comprising (1) converting the organophosphonium compound to an iodide complex of the organophosphonium compound which is insoluble in the organic solvent; and (2) separating the insoluble iodide organophosphonium complex of the organophosphonium compound from the solution. Yet another embodiment of the present invention is a process for the recovery of an organophosphine from a solution of the organophosphine in an organic solvent by the steps comprising (1) converting the organophosphine to an organophosphonium compound; (2) converting the organophosphonium compound to an iodide complex of the organophosphonium compound which is insoluble in the organic solvent; and (3) separating the insoluble iodide complex of the organophosphonium compound from the solution. In the case where the catalyst solution comprises an organophosphine compound one skilled in the art would recognize that the organophosphine may be converted to an organophosphonium iodide compound by the addition of a quaternizing agent, e.g. methyl iodide.

A convenient and efficient means for converting an organophos-phonium iodide compound to an iodide complex of the organophos-phonium compound which is insoluble in the organic solvent comprises the addition of elemental iodine to the solution of the organophos-phonium iodide compound. If the solution containing the dissolved organophosphonium compound also contains one or more iodine-containing compounds (e.g. iodides), the organophosphonium compound may be converted to an insoluble iodide complex of the organophosphonium compound by the addition of an oxidizing agent to the solution of the organophosphonium compound. Alternatively, when the solution contains both dissolved organophosphonium compound and one or more iodine-containing compounds (e.g. iodides), the organophosphonium compound may be converted to an insoluble iodide complex of the organophosphonium compound by the addition of a combination of elemental iodine and an oxidizing agent to the solution of the organophosphonium compound, particularly when insufficient iodide compounds are present in the solution to convert all of the organophosphorus compound to its insoluble iodide complex.

The present invention is particularly useful for the recovery of phosphorous and iodine components from catalyst solutions, especially catalyst solutions used in carbonylation processes such as processes for the production of acetyl products, e.g., acetic acid, acetic anhydride, methyl acetate, ethylidene diacetate, or mixtures of two or more of such acetyl compounds. Carbonylation catalyst solutions typically contain a Group VIII metal (noble or non-noble); iodine compounds, e.g., methyl iodide, phosphine or phosphonium iodide salts, e.g., triphenylphosphine and/or the methyl iodide adduct of triphenylphosphine—methyl(triphenyl)phosphonium iodide; other optional promoters; and an optional solvent, typically an endogenous component such as acetic acid acting as solvent. The phosphonium compound may be prepared ex- or in situ.

One embodiment of the present invention involves the addition of (i) elemental iodine, (ii) an oxidizing agent or (iii)

a combination of (i) and (ii), to a solution, e.g., a catalyst solution, having an organophosphorus compound and, optionally, at least one iodine compound dissolved therein whereby substantial quantities of the organophosphorus compound and, if present, iodine components precipitate from the solution. This treatment allows the separation and recovery of the organophosphorus compounds and iodine components as an insoluble precipitate while other more soluble materials remain in solution. Examples of such more soluble materials may include other phosphonium salts, other catalyst components, unreacted starting materials, reaction products, by-products, other impurities and corrosion metals. Our novel process provides a convenient means for the separation of reusable phosphorus and iodine components from unwanted impurities and contaminants in the catalyst solution.

A further embodiment of the present invention is the reduction of the corrosion metals from the solution. For example, corrosion metals, such as iron and chromium may precipitate from the solution with the insoluble organophosphonium iodide complex. The corrosion metals may be separated from the insoluble organophosphonium iodide complex in another step, such as washing the precipitate.

The phosphorus- and iodine-containing precipitate retrieved as a result of the operation of the present invention may be recycled directly to the carbonylation reactor, or may be redissolved before recycle. It also may be mixed with other fresh or recycled components of the catalyst system and subjected to any necessary processing required prior to returning it to the carbonylation reactor. The solid precipitate may consist, in part, of an organophosphonium triiodide compound which behaves as the functional equivalent of a stoichiometric mixture of the corresponding organophosphonium iodide compound and molecular iodine. However, the precipitate may be a complex mixture of phosphorus- and iodine-containing compounds and this invention relies in no way upon the identification of this material as a organophosphonium triiodide salt. If so desired the precipitate may be further processed or purified, e.g., washing or extracting, prior to reuse.

The use of the invention is simplest when both an organophosphonium compound and one or more iodine-containing compounds (e.g., iodide) are endogenous to the catalyst solution. However, the method also may be used under other circumstances. For example, when the recovery of an organophosphine compound from solution is desired, the organophosphine may first be converted to a phosphonium iodide and then the solution can be treated in accordance with the current invention. Likewise, iodide may be recovered from a solution by the addition of a phosphonium compound followed by treatment as is described here.

The process of the present invention normally does not depend upon the nature of the other components of the catalyst solution and a wide variety of solutions that contain phosphorus and/or iodine compounds (e.g., iodide) may be treated successfully by the process. In certain uses of the invention other components of the solution may co-precipitate with the phosphorus and iodine containing components. This also may be a useful characteristic of the method that would depend upon its particular implementation. In yet another embodiment, the phosphorus- and iodine-containing catalyst components may form compounds that are the more soluble components of the mixture. They then could be separated from the other components by virtue of their remaining in solution. This implementation is also meant to fall within the scope of the disclosed invention.

The present invention is represented by a process for the recovery of an organophosphorus compound such as trihydrocarbylphosphine compounds and tetrahydrocarbylphosphonium compounds from a solution of at least one such organophosphorus compound in an organic solvent by the steps comprising (1) converting the organophosphorus compound to an iodide complex of a tetrahydrocarbylphosphonium compound which is insoluble in the organic solvent; and (2) separating the insoluble iodide complex of the tetrahydrocarbylphosphonium compound from the solution. Examples of such trihydrocarbylphosphine and tetrahydrocarbylphosphonium compounds include compounds having the structures:

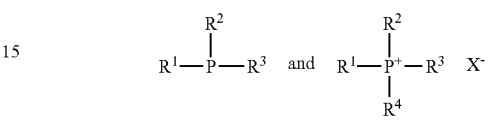

wherein $R^1$, $R^2$, $R^3$ and $R^4$ are independently selected from alkyl, e.g., alkyl, cycloalkyl; aryl such as phenyl and substituted phenyl; and alkoxy, such as —OR; cycloalkoxy; phenoxy, such as —OPh (where O represents oxygen and Ph is a phenyl group and wherein the phenyl group may be substituted), aryloxy, such as —OAr, wherein the Ar is a aryl group; each of the above may be substituted and the substituted portion may include other ligands and/or donor atoms, such as nitrogen, oxygen and/or phosphorus atoms); and $X^-$ is an anion such as a halide, preferably iodide. $R^1$, $R^2$ and $R^3$ are preferably alkyl having 1 to 30 carbon atoms (more preferably 4 to 10 carbon atoms), phenyl or phenyl substituted with alkyl groups. $R^4$ may represent the same substituents which are represented by $R^1$, $R^2$ and $R^3$ but $R^4$ preferably represents lower alkyl, most preferably methyl.

In a preferred embodiment $R^1$, $R^2$ and $R^3$ are selected from phenyl or butyl, $R^4$ is a methyl and $X^-$ is iodide. In a more preferred embodiment, $R^1$, $R^2$ and $R^3$ are equivalent and either phenyl or butyl.

The particular organic solvent used in the process of the present invention is not critical so long as it is inert (nonreactive), is capable of dissolving the trihydrocarbylphosphine or tetrahydrocarbylphosphonium compounds and iodine or iodide compounds, and wherein the tetrahydrocarbylphosphonium iodide complex is insoluble to the extent that it may be substantially separated from the solvent. Examples of such solvents include carboxylic acids and their anhydrides, e.g., $C_2$ to $C_4$ aliphatic carboxylic acids or anhydrides; alkyl esters of aliphatic and aromatic, mono- and di-carboxylic acids containing up to about 8 carbon atoms.

The conversion of the soluble tetrahydrocarbylphosphonium compound to its insoluble iodide complex, e.g., triiodide, may be carried out over a wide range of temperatures and pressures, e.g., at temperatures in the range of about ambient to 150° C. and pressures in the range of about 0 to 15 bar gauge (barg). Preferred conditions comprise temperatures in the range of about ambient to about 110° C. and pressures in the range of about 0 to about 5 barg. Likewise, the temperature at which precipitation and collection of the insoluble iodide complex is carried out can vary over a wide range and such conditions are not a critical feature of the invention. One skilled in the art would understand that it may be advantageous to hold the mixture containing the insoluble iodide complex at as low a temperature as necessary to induce efficient recovery of the solids. The temperature employed will be above the freezing point of the mixture. The isolation/recovery temperature may vary from about 0 to about 110° C., preferably from about 0 to about 50° C.

The insoluble iodide complex may be formed by contacting the tetrahydrocarbylphosphonium compound (wherein X– is iodide) with molecular iodine. Such contacting may be accomplished by the addition of molecular iodine, either as a solid or as a solution in a solvent that is compatible or miscible with the organic solvent in which the tetra-hydrocarbylphosphonium compound is dissolved. This embodiment of our invention involves a process for the recovery of a tetra-hydrocarbylphosphonium compound from a solution, e.g., a catalyst solution, of a tetrahydrocarbylphosphonium compound (wherein X– is iodide) in an inert, organic solvent which comprises the steps of (1) adding molecular iodine to the solution in an amount sufficient to convert the tetrahydrocarbylphosphonium compound to an iodide complex of the tetrahydrocarbylphosphonium compound which is insoluble in the organic solvent; and (2) separating the insoluble iodide complex from the solution. The amount of molecular iodine provided to the organic solution containing the tetrahydrocarbylphosphonium compound should give a total iodine:phosphorus atomic ratio of at least 3:1, wherein the phosphorus is provided by the tetrahydrocarbylphosphonium compound.

Alternatively, the molecular iodine with which the tetrahydrocarbylphosphonium compound is contacted may be derived, totally or in part, from dissolved iodide ion present in the solution of the organic tetrahydrocarbylphosphonium compound by contacting the iodide-containing organic solution with an oxidizing agent. This embodiment of the invention involves contacting a solution comprising a tetrahydrocarbylphosphonium compound and an iodide compound dissolved in an inert, organic solvent with an oxidizing agent to convert the tetrahydrocarbylphosphonium compound to an iodide complex of the tetrahydrocarbylphosphonium compound which is insoluble in the organic solvent; and (2) separating the insoluble iodide complex from the solution. In this embodiment of our invention, the oxidizing agent converts dissolved iodide ions to molecular iodine which reacts with the tetrahydrocarbylphosphonium compound to convert it to an iodide complex of the tetrahydrocarbylphosphonium compound which is insoluble in the organic solvent.

Examples of suitable oxidizing agents include molecular oxygen-containing gases such as oxygen, air and oxygen-enriched air; and peroxides such as hydrogen peroxide and percarboxylic acids such as peracetic acid; and ozone. The amount of the oxidizing agent that is required can be determined readily by those skilled in the art. The source of the dissolved iodide ion can be various iodide compounds and/or salts which are utilized in catalyst solutions, particularly catalyst solutions used in the manufacture of acetyl compounds. Examples of such iodide sources include hydrocarbyl iodides, e.g., alkyl iodides containing up to about 6 carbon atoms, particularly methyl iodide, and inorganic iodide salts used as catalyst promoters such as alkali metal and alkaline earth metal iodides, chromium, molybdenum and tungsten iodides. It will be apparent to those skilled in the art that sufficient iodide ion must be present and sufficient oxidizing agent must be used to convert the tetrahydrocarbylphosphonium compound to an iodide complex of the tetrahydrocarbylphosphonium compound which is insoluble in the organic solvent. If insufficient iodide ion is present and/or insufficient oxidizing agent is employed, more complete recovery of the tetrahydrocarbylphosphonium compound may be obtained by the addition of iodide or iodine, or additional oxidizing agent.

The present invention provides a method for the recovery of phosphorus and iodine components from catalyst solutions used in the production of acetyl compounds such as acetic acid and other organic compounds. However, the preferred mode of operating the present invention involves the recovery of both phosphorus and iodine components (which may include iodide) from catalyst solutions used in carbonylation processes for the manufacture of acetyl compounds, especially carbonylation processes wherein a mixture of methanol and methyl iodide are contacted with carbon monoxide in the presence of a catalyst system to produce acetic acid. The catalyst system comprises a Group VIII non-noble metal, e.g., nickel, and an organophosphorus promoter (which is present primarily as a phosphonium iodide salt) and, optionally, an additional promoter, e.g., a molybdenum compound. Such carbonylation processes normally are carried out in the liquid phase comprising acetic acid or a mixture comprising acetic acid and water as the process solvent. Thus, the preferred mode of utilizing the present invention involves a process for the recovery of both phosphorus and iodine components from a catalyst solution comprising a Group VIII non-noble metal, methyl iodide and a tetrahydrocarbylphosphonium iodide dissolved in a process solvent comprising acetic acid or a mixture comprising acetic acid and water which comprises the steps of (1) converting the tetrahydrocarbyl-phosphonium iodide to an iodide complex of the tetrahydrocarbylphosphonium iodide which is insoluble in the process solvent; and (2) separating the insoluble iodide complex of the tetrahydrocarbylphosphonium iodide from the solution.

Commercial carbonylation processes are operated continuously for extended periods of time. During such prolonged operation under commercial conditions, catalyst solutions become contaminated with undesirable impurities which either arise as byproducts of the desired reaction or appear as the products of corrosion or decomposition of various catalyst components. Some of these impurities may be carried to downstream processing steps where they are separated from the desired reaction products and discarded. Others, through the action of integrated recycle steps or because they never escape, accumulate and steadily increase in concentration in the environs of the reactor. Under these circumstances it is usual to continually remove a small portion of the catalyst or process solution and discard it as a means of controlling the buildup of such impurities. Fresh catalyst solution may be added to the process in order to compensate for the loss of this small catalyst purge.

Unfortunately, such a catalyst purge stream usually contains economically-valuable catalyst components or components which cause pollution of the environment if this stream is not treated. The objective of the present invention is to provide a means for recovery of valuable catalyst components, i.e., phosphorus-iodine compounds.

The following steps illustrate an embodiment of the invention, which is the operation of the invention in conjunction with a carbonylation process for the production of acetic acid.

Recovery by Addition of Iodine and an Oxidizing Agent (1) A portion of catalyst/process solution, e.g., a catalyst purge stream, is removed from the process and if desired, the solution is concentrated by removing some of the volatile components by distillation.

(2) The solution from (1) is stirred and iodine is added, either as a solid or as a solution in an appropriate solvent, whereby a precipitate forms. If desired, the precipitate may be recovered at this point. ( 3) The mixture then is treated with an oxidizing agent such as air or hydrogen peroxide.

(4) The precipitate obtained in (2) and (3) is separated, e.g., by filtration or centrifugation or decantation, from the solution phase and the solution phase may be discarded or subjected to further processing.

(5) The precipitate may be washed to effect further purification and then may be redissolved or slurried to ease further handling.

(6) The solution, slurry, or solids containing recovered catalyst components obtained in (5) may be recycled directly to the reactor or may be combined with additional fresh catalyst components.

(7) Optionally, the solution containing recycled catalyst components (the precipitate) and optionally fresh catalyst components may be subjected to a preactivation step before being recycled to the reactor.

Recovery by Addition of Oxidizing Agent

Preceding steps (1)-(7) may be modified so that in (2) and (3) only an oxidizing agent is added whereby a precipitate forms. Iodine is not added.

Recovery by Addition of Iodine

Preceding steps (1)-(7) may be modified so that in (2) and (3) iodine is added whereby a precipitate forms. An oxidizing agent is not added.

The operation of the process of the present invention is further illustrated by the following examples. One should understand that the examples cited are only illustrative and not limiting. Other embodiments of the invention also fall within its scope.

In a commercial carbonylation process for the manufacture of acetic acid, methanol, methyl iodide, water, carbon monoxide, a catalyst recycle stream comprising acetic acid and dissolved catalyst components and, optionally, hydrogen are fed continuously to a reactor. The reactor is maintained at an elevated temperature and pressure that results in a liquid phase reaction medium. A crude, liquid product stream comprising acetic acid and dissolved catalyst components is removed continuously from the reactor and fed to a flash evaporator. There, as result of reducing the pressure, up to about 70 weight percent of the liquid product stream is vaporized. The non-vaporized portion of the liquid product stream comprising acetic acid, water, methyl iodide, methyl acetate, methanol, non-volatile catalyst components and impurities is recycled to the carbonylation reactor (the catalyst recycle stream). Fresh catalyst components are added to the process as needed to maintain a predetermined concentration of the components. The liquid product vaporized in the flash evaporator is fractionated into acetic acid product that is removed from the process and low boiling components such as methanol, methyl iodide and methyl acetate which are recycled to the carbonylation reactor.

Typically, a small portion of the catalyst recycle stream, e.g., from about 0.001% to about 1%, is removed continuously from the process. Discarding this material, the catalyst purge stream, allows the concentrations of undesirable impurities in the reactor to be maintained at acceptable levels. Although a portion of the crude product stream that is fed to the flash evaporator may be removed as the catalyst purge stream, a portion of the stream exiting the flash evaporator is the preferred purge stream since it is more highly concentrated in non-volatile catalyst components and impurities. If desired, distillation may be used to remove additional volatile components from either of these streams before further treatment. These removed additional volatile components may also be recycled to the process.

The composition of the predominantly liquid phase stream being treated may vary over wide limits and is not important to the successful practice of the current invention. The only requirement is that the stream contains sufficient concentrations of the organophosphorus compound (typically a tetrahydrocarbylphosphonium iodide) and iodide species so that they form an insoluble complex which precipitates from solution when the invention is practiced. Since the catalyst purge stream is removed from the process, it is apparent that the concentration of compounds in that stream may be varied independently of any other process requirement. One skilled in the art will understand that precipitation relies upon the presence of enough compound to exceed that compound's solubility in the solvent being used and, furthermore, that the concentrations may be adjusted to ensure adequate recovery of solids from the catalyst purge stream. The composition of the catalyst purge stream would be consistent with the process requirements for efficient operation of the reactor such as those set forth in U.S. Pat. Nos. 4,661,631, 4,659,518 and 4,356,320 and Published British Patent Application 2,121, 794A. The method of the current invention may be operated in a continuous, semi-continuous or batch fashion.

EXAMPLE 1

A stirred autoclave constructed of Hastelloy B-2 alloy and having a working volume between 400 and 1200 mL was operated batchwise as both the reactor and flash separator for the carbonylation of methanol to acetic acid. The autoclave was fitted with two dip tubes that were connected via valves to a jacketed condenser where samples of the liquid carbonylation mixture could be collected. The tip of the dip tubes was located approximately two inches from the bottom of the autoclave. A mixture of 385 mL of methanol, 80 mL of methyl acetate, 123 mL of methyl iodide, 254 mL of acetic acid, 72 mL of water, 10.6 grams of nickel acetate, 9.0 grams of molybdenum hexacarbonyl, and 86.1 grams of triphenylphosphine were charged to the autoclave. The vessel was pressure tested with carbon monoxide from a surge tank and then was pressurized twice with carbon monoxide to 13.8 barg and vented to purge nitrogen and oxygen. The vessel was agitated vigorously while adding 34.5 barg of carbon monoxide and 6.9 barg of hydrogen. The contents of the autoclave were then heated to 200° C. before carbon monoxide was added to pressurize the system to 89.6 barg. Carbon monoxide was added slowly throughout the reaction to maintain a pressure of 89.6 barg, and the temperature was controlled at 200° C. for five hours. The contents of the autoclave were then cooled to 150° C. and periodically vented to 3.4 barg until the temperature and pressure were stabilized. Then, the contents of the autoclave were cooled to 100° C. Agitation was continued throughout the entire carbonylation. The carbon monoxide uptake was measured and compared to the theoretical value for the carbonylation to assure that the reaction occurred as planned. After the carbonylation had been completed, a sample of the carbonylation liquid was collected through the dip tube.

Oxidation of the carbonylation liquid in the autoclave then commenced. Hydrogen peroxide (200 mL of 30% in water) was added to the autoclave through a blowcase, and the temperature was maintained at 100° C. Agitation of the mixture was maintained throughout the oxidation. A second sample of the carbonylation liquid was then withdrawn through the dip tube twenty-four hours after the hydrogen peroxide had been added. The oxidized carbonylation mixture was then cooled to 25° C. under pressure, and it was sampled for a third time through the dip tube. Finally, the pressure was relieved to atmospheric conditions and a final sample of the oxidized carbonylation liquid was collected. The oxidized carbonylation slurry was then discharged to a vessel and held at 0° C. until it was filtered. The carbonylation slurry consisted of a dark brown liquid phase and a solid phase that was a black crystalline material. The masses of the filtrate and solids were 545 and 836 grams, respectively. The solids and liquids were analyzed for phosphorus, total iodine, nickel, molybdenum, iron, and chromium via Phosphorus 31 Nuclear Magnetic Resonance Spectroscopy and ICP analysis. The percent recovery for these components in the solid phase was computed by dividing the mass of the component of interest in the solid phase by the mass of the component in the total slurry. The percent recovery for phosphorus, iodine, molybdenum, nickel, iron, and chromium were 95.7, 90.2, 96.3, 57.5, 87.2, and 59.0, respectively. The solids, which were black and crystalline, were analyzed and determined to contain methyltriphenylphosphonium triiodide, among other compounds. Therefore, a significant amount of the phosphorus and iodine components of the catalyst solution were recovered to a solid form for recovery and recycle to the carbonylation reactor.

EXAMPLE 2

Fifty grams of the black crystalline solids from Example 1 were placed atop a filter medium and washed with 50 grams of water for one minute with continuous stirring. The wash water was then separated from the solids via filtration. This wash procedure was repeated nine additional times with fresh water. Both the original solids and those solids that had been washed ten times with water were analyzed by Phosphorus 31 NMR, and ICP for iron, nickel, molybdenum, chromium, total iodine, and phosphorus. The percent removal of molybdenum, nickel, iron and chromium from the solids after washing was 98, 86, 87, and 82%, respectively, based on the original solids. The percent losses of iodine and phosphorus were only 3 and 5%, respectively. Therefore, many of the catalyst and corrosion metals could be separated from the phosphorous- and iodine-containing solids by washing with water.

EXAMPLE 3

A stirred autoclave constructed of Hastelloy B-2 alloy with a working volume between 400 and 1200 mL was operated batchwise as both the reactor and flash separator for the carbonylation of methanol to acetic acid. The autoclave was fitted with two dip tubes that were connected via valves to a jacketed condenser where samples of the liquid carbonylation mixture could be collected. The tip of the dip tubes was located approximately two inches from the bottom of the autoclave. A mixture containing 322 mL of methanol, 67 mL of methyl acetate, 55.4 mL of methyl iodide, 212.6 mL of acetic acid, 60 mL of water, 8.9 grams of nickel acetate, 7.5 grams of molybdenum hexacarbonyl, 146 grams of triphenylphosphine, 14.4 grams of chromium acetate, and 3.11 grams of iron acetate was charged to the autoclave. The vessel was pressure tested with carbon monoxide from a surge tank and then pressurized twice with carbon monoxide to 13.8 barg and vented to purge nitrogen and oxygen. The vessel was vigorously agitated while adding 34.5 barg of carbon monoxide and 6.9 barg of hydrogen. The contents of the autoclave were then heated to 200° C. before carbon monoxide was added to pressurize the system to 89.6 barg. Carbon monoxide was added slowly throughout the reaction to maintain a pressure of 89.6 barg and the temperature was controlled at 200° C. for a period of ten hours. The contents of the autoclave were cooled to 150° C. and periodically vented to 3.4 barg until the temperature and pressure were stabilized for four hours. Agitation was continued throughout the entire carbonylation. The carbon monoxide uptake was measured and compared to the theoretical value for the carbonylation to assure that the reaction occurred as planned. After the carbonylation had been completed, a sample of the carbonylation liquid was collected through the dip tube. Then the solution was cooled to 25° C., and the resultant slurry was filtered through a Buchner funnel to yield 975.1 grams of filtrate and 222.3 grams of solids. The recovery of iodine and phosphorus in the solid phase was 43.6% and 32.8%, respectively, in this first precipitation. The filtrate was subsequently charged to a glass, 2-liter, round-bottomed flask.

Oxidation of the carbonylation liquid in the flask then commenced. Laboratory-grade air was bubbled through the liquid for a period of twenty-four hours. Then the slurry was filtered to yield 66.3 grams of solids and 440 grams of filtrate. The latter was returned to the round-bottomed flask with 100 grams of iodine crystals. This adjusted the stoichiometric iodine to phosphorus ratio in the flask to three. Laboratory-grade air was again bubbled through this liquid for twenty-four hours. The resulting slurry was filtered to produce 375 grams of filtrate and 157 grams of solids. Recovery in the solid phases from the precipitation, oxidation, and iodine addition for phosphorus, iodine, molybdenum, nickel, iron, and chromium were 87.4, 98.9, 69.9, 68.9, 98.2, and 26.3%, respectively.

EXAMPLE 4

A stirred autoclave constructed of Hastelloy B-2 alloy having a working volume between 400 and 1200 mL was operated batchwise as both the reactor and flash separator for the carbonylation of methanol to acetic acid. The autoclave was fitted with two dip tubes that were connected via valves to a jacketed condenser where samples of the liquid carbonylation mixture could be collected. The tip of the dip tubes was located approximately two inches from the bottom of the autoclave. A mixture containing 322 mL of methanol, 67 mL of methyl acetate, 55.4 mL of methyl iodide, 212.6 mL of acetic acid, 60 mL of water, 8.9 grams of nickel acetate, 7.5 grams of molybdenum hexacarbonyl, 146 grams of triphenylphosphine, 14.4 grams of chromium acetate, and 3.11 grams of iron acetate was charged to the autoclave. The vessel was pressure tested with carbon monoxide from a surge tank. The vessel was then pressurized twice with carbon monoxide to 13.8 barg and vented to purge nitrogen and oxygen. The vessel was vigorously agitated while adding 34.5 barg of carbon monoxide and 6.9 barg of hydrogen. The contents of the autoclave were then heated to 200° C. before carbon monoxide was added to pressurize the system to 89.6 barg. Carbon monoxide was added slowly throughout the reaction to maintain a pressure of 89.6 barg and the temperature was controlled at 200° C. for ten hours. The contents of the autoclave were cooled to 150° C. and periodically vented to 3.4 barg until the temperature and pressure were stabilized for four hours. Agitation was continued throughout the entire carbonylation. The carbon monoxide uptake was measured and compared to the theoretical value for the carbonylation to assure that the reaction occurred as planned. After the carbonylation had been completed, a sample of the carbonylation liquid was collected through the dip tube. The iodine and phosphorus concentrations were found to be 4.6 and 0.98 weight percent, respectively. Then the solution was cooled to 30° C. and was transferred to a nitrogen purged autoclave constructed of Hastelloy C alloy that contained 223 grams of iodine. The atomic ratio of iodine to phosphorus in the slurry after the transfer was three. This slurry was held without agitation at 25° C. for a period of ten hours. The solution was then filtered through a Buchner funnel to yield 530.4 grams of filtrate and 241.6 grams of solids. The solids contained 64% of the iodine and 56% of the phosphorus. The filtrate, which contained 4.83% iodine and 0.15% phosphorus, was then charged to a glass 2-liter round-bottomed flask. Air was bubbled through this liquid for a period of 24 hours before the slurry was again filtered. The filtration resulted in 357.12 grams of filtrate and 114.0 grams of solids. The overall iodine and phosphorus recovery in the solid phases was 90.2% and 98.1%, respectively.

The invention has been described in detail with particular reference to preferred embodiments thereof, but it will be understood that variations and modifications will be effected within the spirit and scope of the invention.

We claim:

1. Process for the recovery of an organophosphorus compound from a solution of at least one such organophosphorus compound and an iodine-containing compound in an organic solvent comprising the steps of (1) adding an oxidizing agent and elemental iodine to the solution to convert the organophosphorus compound to an iodide complex which is insoluble in the organic solvent; and (2) separating the insoluble iodide complex from the solution;

wherein the organophosphorus compound is tetrahydrocarbylphosphonium and has the structure:

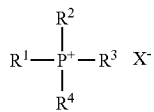

wherein $R^1$, $R^2$, $R^3$ and $R^4$ are independently selected from alkyl, phenyl, cycloalkyl, aryl, alkoxy, cycloalkoxy, phenoxy and aryloxy; and wherein $X^-$ is a halide.

2. Process according to claims 1 wherein the organophosphorus compound is tetrahydrocarbylphosphonium.

3. Process for the recovery of an organophosphorus compound compounds from a solution of at least one such organophosphorus compound and an iodine-containing compound in an organic solvent comprising the steps of (1) adding elemental iodine to the solution to convert the organophosphorus compound to an iodide complex which is insoluble in the organic solvent; and (2) separating the insoluble iodide complex from the solution;

wherein the organophosphorus compound is tetrahydrocarbylphosphonium and has the structures:

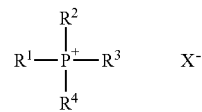

wherein $R^1$, $R^2$, $R^3$ and $R^4$ are independently selected from alkyl, phenyl, cycloalkyl, aryl, alkoxy, cycloalkoxy, phenoxy and aryloxy; and wherein $X^-$ is a halide.

4. Process according to claim 3 wherein the alkyl has 1 to 30 carbons.

5. Process according to claim 3 wherein the alkyl has 4 to 10 carbons.

6. Process according to claim 3 wherein $R^1$, $R^2$ and $R^3$ are selected from butyl and phenyl.

7. Process for the recovery of phosphorus and iodine components from a catalyst solution comprising a Group VIII non-noble metal, methyl iodide and a tetrahydrocarbylphosphonium iodide dissolved in a process solvent comprising acetic acid or a mixture of acetic acid and water which comprises the steps of (1) adding molecular iodine to the catalyst solution and converting the organophosphonium iodide to an iodide complex of the organophosphonium iodide which is insoluble in the process solvent; and (2) separating the insoluble iodide complex of the organophosphonium iodide from the solution;

wherein the tetrahydrocarbylphosphonium iodide has the structure:

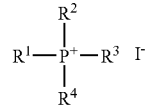

wherein $R^1$, $R^2$ and $R^3$ are selected from butyl and phenyl; and wherein $R^4$ is a methyl.

8. Process according to claim 7 wherein step (1) includes adding an oxidizing agent to the catalyst solution.

9. Process according to claim 8 wherein that oxidizing agent is oxygen, air, oxygen-enriched air, hydrogen peroxide, ozone or peracetic acid.

10. Process according to claim 7, further comprising recycling the insoluble iodide complex to the catalyst solution.

* * * * *